United States Patent [19]

Aoyagi et al.

[11] Patent Number: 5,759,849
[45] Date of Patent: Jun. 2, 1998

[54] SLUDGE TREATMENT TANK THEREOF CONSTRUCTION METHOD THEREOF

[75] Inventors: Keitaro Aoyagi, Kawasaki; Sadao Niibe, Chiba; Toshitomi Umegae, Sakura; Hideo Iwai, Oumihachiman; Yoshitugu Oshima, Tokyo, all of Japan

[73] Assignees: The Zenitaka Corporation; Sekisui Kagaku Kogyo Kabushiki Kaisha, both of Japan

[21] Appl. No.: 876,300

[22] Filed: Jun. 16, 1997

Related U.S. Application Data

[62] Division of Ser. No. 610,252, Mar. 4, 1996, Pat. No. 5,672,506.

[30] Foreign Application Priority Data

Mar. 9, 1995 [JP] Japan .................... 7-49555

[51] Int. Cl.⁶ .................................. C12M 3/00
[52] U.S. Cl. .................... 435/289.1; 52/169.3; 52/309.4; 52/309.7; 52/309.8; 52/309.12; 249/13; 249/15; 249/189; 249/207
[58] Field of Search ............... 435/289.1, 290.1; 52/169.7, 309.1, 309.4, 309.7, 309.8, 309.9, 309.12, 309.17; 249/13, 15, 1, 187.1, 189, 207; 210/167

[56] References Cited

U.S. PATENT DOCUMENTS

| | | | |
|---|---|---|---|
| 4,252,767 | 2/1981 | Piazza et al. | 264/256 |
| 5,105,590 | 4/1992 | Dykmans | 52/741 |
| 5,315,872 | 5/1994 | Moser | 73/304 C |

OTHER PUBLICATIONS

Faulbehalter aus Beton. Sonderdruck aus Bauingenieur 54 (1979) pp. 77–84.

*Primary Examiner*—David A. Redding
*Attorney, Agent, or Firm*—Heslin & Rothenberg, P.C.

[57] ABSTRACT

In a sludge treatment tank, members made of a glass long-fiber reinforced foamed plastic composite material are used as formworks in construction and then left as an inside wall member. The composite material functions as formworks in a construction method as well as applies an insulating property and a corrosion resistant property to the sludge treatment tank and further realizes labor saving in a field of construction works, the provision of a good working environment and the reduction of a period of construction work.

5 Claims, 9 Drawing Sheets

SLUDGE TREATMENT TANK THEREOF CONSTRUCTION METHOD THEREOF

This application is a division of application Ser. No. 08/610,252 filed Mar. 4, 1996 which is now, U.S. Pat. No. 5,672,506.

BACKGROUND OF THE INVENTION

1. Field of the Invention

The present invention relates to a sludge treatment tank and a construction method thereof, and more specifically, to a sludge treatment tank suitable for a biological reaction tank such as a digester tank and the like for the treatment of sludge in a sewage treatment plant and a construction method thereof.

2. Description of the Related Art

In general, sludge contained in inflow sewage is separated from water by a sedimentation treatment or the like, organic substances contained in the separated sludge are removed as a gas by a biological reaction effected in a digester tank having an optimum temperature and the remaining sludge is disposed of by being dehydrated, dried and burnt. The organic gas taken out is used as an energy source by being burnt.

At present, there are constructed three types of tanks having considerably different longitudinal cross sectional shapes as the digester tank (refer to Concrete Digester Tank - I in "Environment Technology" published by Environmental Technology Research Institute, March 1982, pages 71–75, translated by Keitaro Aoyagi).

Figure 10:
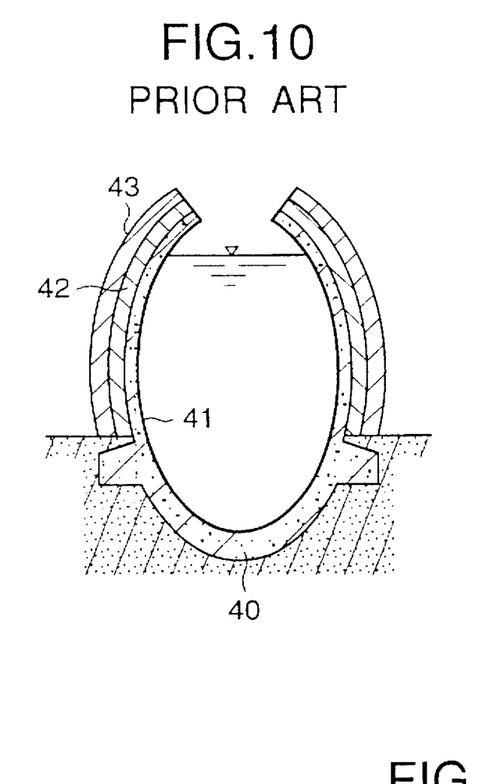
FIG. 10 is a longitudinal cross sectional view showing an example of a conventional egg-shaped digester tank.
Figure 11:
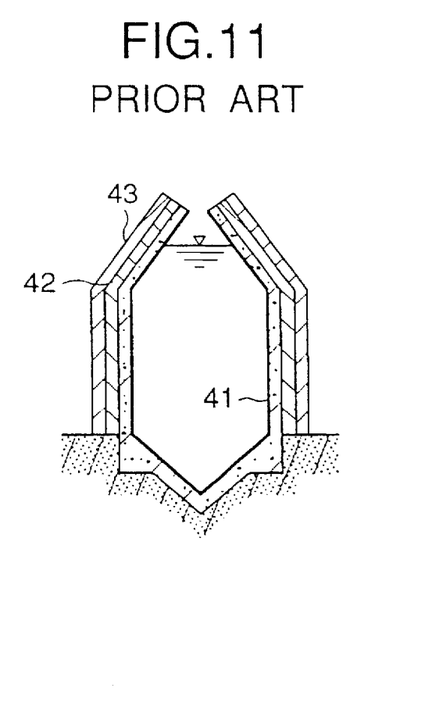
FIG. 11 is a longitudinal cross sectional view showing an example of a conventional hexagon-shaped digester tank.
Figure 12:
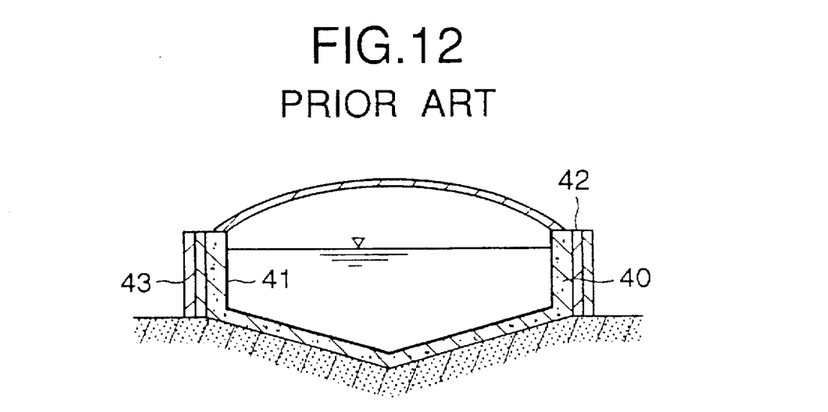
FIG. 12 is a longitudinal cross sectional view showing an example of a conventional flat digester tank.

FIG. 10–FIG. 12 show these three types of the digester tanks, wherein FIG. 10 shows a tank having an egg-shaped longitudinal cross sectional shape, FIG. 11 shows a tank having a hexagon-shaped longitudinal cross sectional shape and FIG. 12 shows a tank having a flat longitudinal cross sectional shape. The flat tank formed to a cylindrical shape with a large diameter shown in FIG. 12 has a defect that it requires a large exclusive area, is disadvantageous in heat accumulation and operates at an expensive running cost. The egg-shaped tank shown in FIG. 10 makes sludge to smoothly circulate and flow, has a small exclusive area and operates at a low running cost because the tank can be easily insulated. Although the hexagon-shaped tank shown in FIG. 11 is somewhat inferior to the egg-shaped tank in performance, since it does not include such complex curves as used in the egg-shaped tank, it can be easily constructed. In Europe and the United States, a great many number of the egg-shaped tanks of FIG. 10 or the hexagon-shaped tanks of FIG. 11 are constructed.

As shown in FIG. 10–FIG. 12, these digester tanks are constructed such that a corrosion preventing material 41 is coated on the inside wall of a reinforced concrete 40 and a heat insulator 42 and further a weather lining 43 is applied on the outside thereof. In this construction method, it is a usual practice that after reinforcing bars are fabricated, formworks are applied on the outside and the inside of the reinforcing bars and concrete is placed and a prestress is applied by high strength steel members. Further, the heat insulator is applied on the outside wall of the concrete for heat insulation and the weather lining is applied for finishing the outside of the concrete. Further, a corrosion preventing material is coated on the inside wall surface and thereafter machinery and equipment, pipings are installed in the tank.

However, the above conventional technology has the following problems:

(1) scaffolds are necessary on the inside and the outside;

(2) a heat insulator must be applied on the outside wall surface for heat insulation and further exterior finishing must be executed to provide durability to rain and water;

(3) a corrosion preventing work must be executed to a concrete inside wall surface using thinner and the like in a closed working environment to use the tank as a sludge tank;

(4) a troublesome and time-consuming job is needed to fabricate and remove formworks in a concrete work; and (5) a heat insulation work, exterior work and corrosion preventing work cannot be executed before a concrete structure is finished.

SUMMARY OF THE INVENTION

An object of the present invention for solving the above problems is to provide a sludge treatment tank capable of realizing labor saving in working processes in a field of construction work, reduction of a period of construction work and working in a good environment as well as a method of constructing the sludge treatment tank in the construction of a biological reaction tank such as a digester tank and the like. The sludge treatment tank of the present invention comprises a concrete tank including a member composed of a glass long-fiber reinforced foamed plastic composite material as an inside wall material also serving as a formwork.

Further, the above object can be achieved by a method of constructing a sludge treatment tank, comprising the step of using a member composed of a glass long-fiber reinforced foamed plastic composite material as the inside formworks of inside and outside formworks used to place concrete to the concrete sludge treatment tank.

According to the above arrangement, since the glass long-fiber reinforced foamed plastic composite material has strength similar to or greater than that of wood, it can be used as a formwork, thus the composite material can be used as an inside wall member also serving as the formwork. Moreover, since the composite material contains closed cells and has heat insulating property, it is effective as an insulating material. Further, since the composite material is composed of a plastic material, it has a corrosion preventing action because it does not have a water absorbing property and is resistant to acid and alkali.

Consequently, when the composite material is used as an inside wall member also serving as a formwork, a heat insulator and a corrosion preventing material, inside scaffolds are not needed and an insulating work, weather lining work and inside wall surface corrosion preventing work can be omitted. Further, the interior of the tank can be kept to a good working environment by the omission of the corrosion preventing work.

Further, since the above glass long-fiber reinforced foamed plastic composite material is light in weight and can be easily handled, labor can be saved and a working efficiency can be improved in a field work.

DESCRIPTION OF PREFERRED EMBODIMENT

Figure 1:
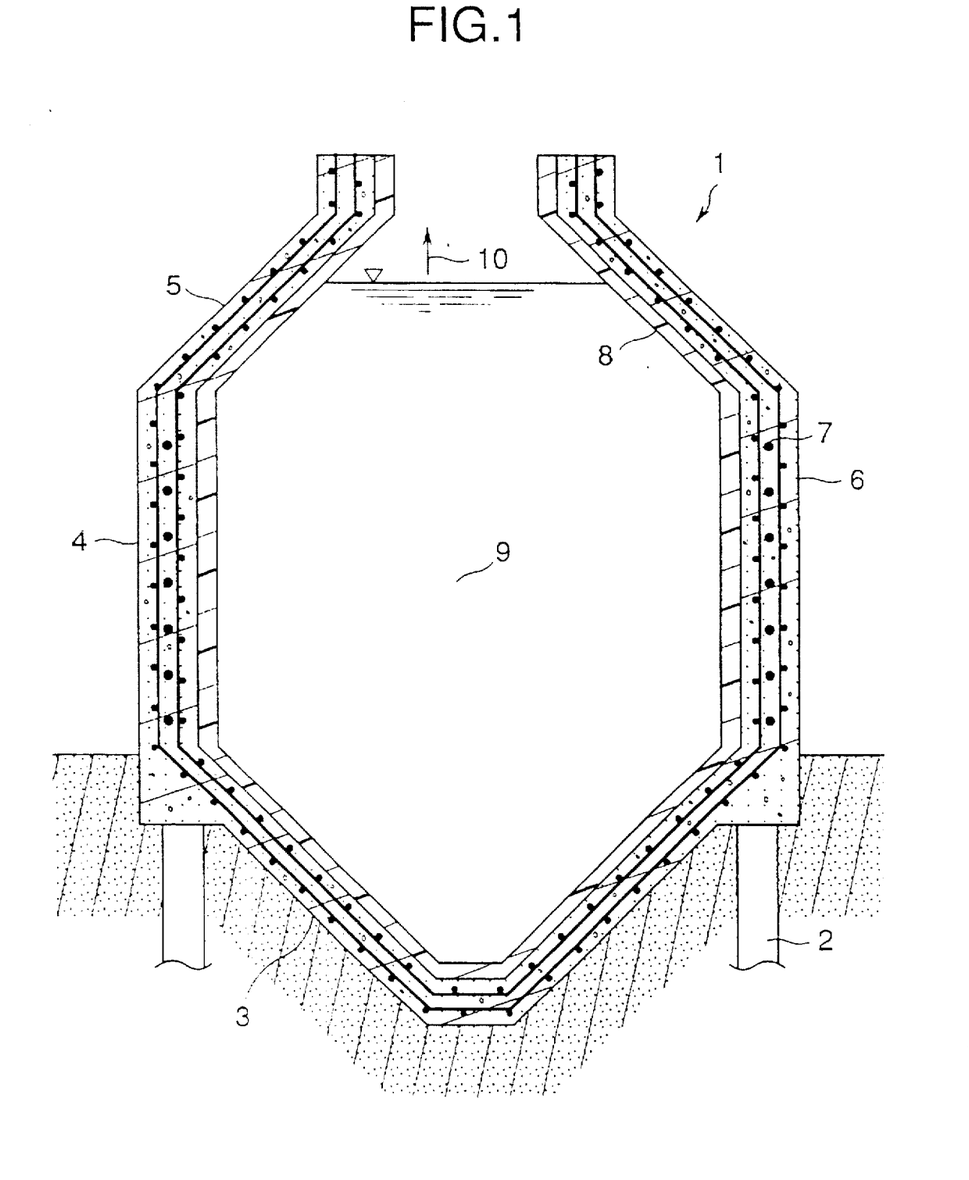
FIG. 1 is a longitudinal cross sectional view showing a digester tank of an embodiment of the present invention.

An embodiment of the present invention will be described with reference to the drawings. A digester tank 1 of an embodiment according to the present invention includes a hexagon-shaped longitudinal cross section composed of a lower conical portion 3, a cylindrical sidewall portion 4 and an upper conical portion 5 supported by stakes 2. A tank wall 6 is composed of a reinforced concrete and applied with a prestress by high strength steel members 7.

An outside wall is finished by placed concrete and an inside wall member 8 of the tank is formed of a glass long-fiber reinforced formed urethane (hereinafter, abbreviated as GFRU) composite material.

That is, an example of the GFRU composite material is a formed urethane resin material with a specific gravity in a range of 0.30–0.80 composed of 65–45 wt % of an urethane resin and 35–55 wt % of glass longfibers (preferably, woven glass roving) in a composition ratio. It is more preferable from a view point of balance between strength and economic efficiency that the foamed urethane resin material is composed of 60–55 wt % of an urethane resin and 40–45 wt % of glass long-fibers and has a specific gravity of a range of 0.40–0.60.

Note, saturated or unsaturated ester resin and thermoplastic foamed resin such as epoxy resin may be used as the foamed plastic material in addition to the urethane resin, and carbon fibers or organic fibers such as aramid fibers may be used as the reinforcing material in addition to the glass long-fibers. The aforesaid composite material is light in weight and excellent in dimensional stability, resistance to water absorption, durability, nail-holding power, wear resistance and impact resistance.

Since the above GFRU member can be used as a member also serving as a formwork member, a heat insulator and a corrosion resistant member, the GFRU member is used as the inside wall member 8 which also serves as a formwork when concrete is placed.

There is commercially available "Eslon Neo Lumber FFU" (trade name of Sekisui Chemical Co., Ltd.) as a GFRU product. Further, when a foamed urethane resin with a specific gravity of 0.35 which is composed of 60 wt % of an urethane resin and 40 wt % of glass long-fibers and has at least one surface covered with a water-proof layer (thickness: about 0.5 mm) composed of an unfoamed urethane resin containing a glass fiber mat and the like is used, a cost is further reduced and resistance to water absorption and wear resistance can be more improved.

When the tank constructed as described above is filled with sewage sludge 9 and is kept to a temperature of about 35° C., organic substances in the sludge are dissolved by anaerobes in the tank and a methane gas 10 is generated. The thus generated methane gas can be used as an energy source by being burnt. The sludge from which the organic substances are removed is disposed of by being dehydrated and dried.

Next, a method of constructing the digester tank shown in FIG. 1 will be described.

(1) First, the execution of works for the lower conical portion will be described.

Figure 2:
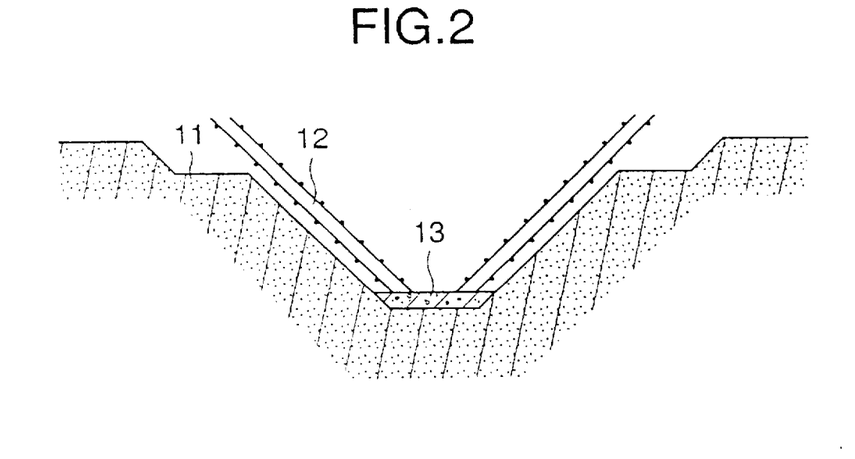
FIG. 2 is a longitudinal cross sectional view showing a part of a lower conical portion constructed by a method of the present invention.

As shown in FIG. 2, the ground 11 is excavated, reinforcing bars 12 are disposed and a bottom concrete 13 is placed.

Figure 3:
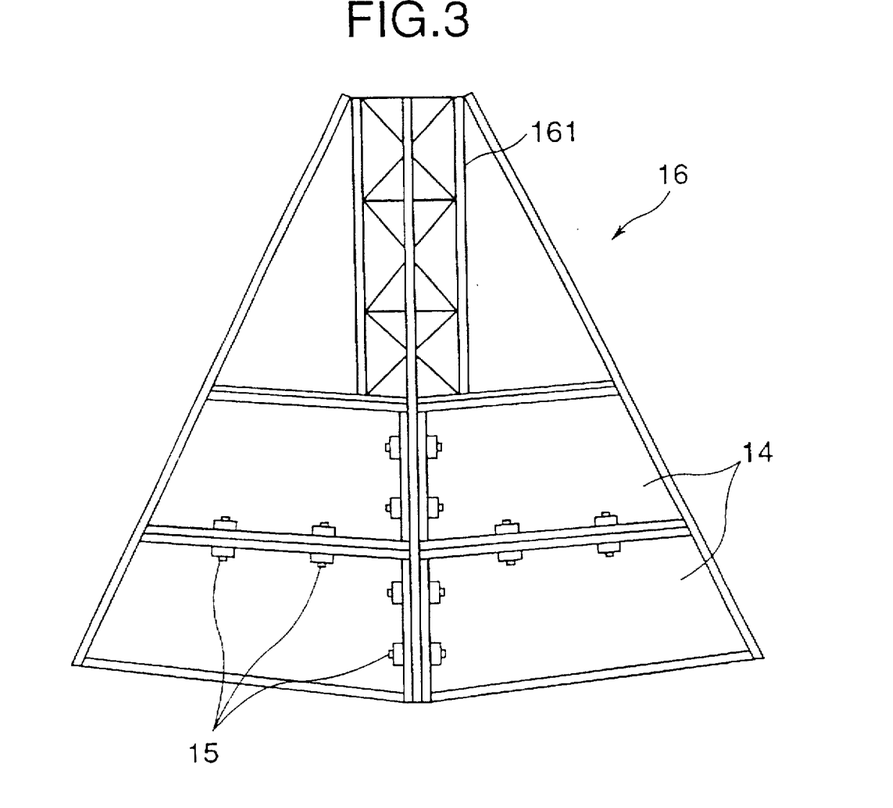
FIG. 3 is a conceptual view of conical inside wall members fabricated by the method of the present invention.
Figure 4:
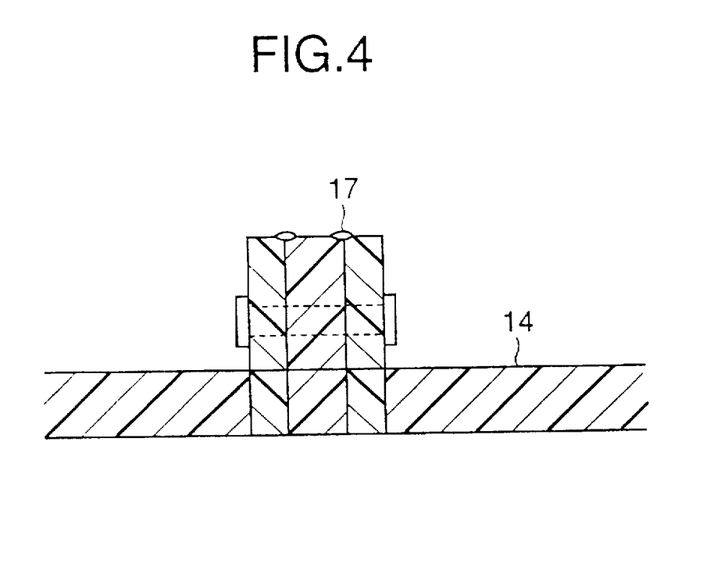
FIG. 4 is a detailed view of a portion where panels are jointed by the method of the present invention.

As shown in FIG. 3, GFRU panels 14 made in a factory are fabricated to a conical shape by a jig 161 using bolts 15, nails or an adhesive to make a conical inside wall member 16. In this case, joints 17 are sealed with a resin, tape or adhesive as shown in FIG. 4.

Figure 5:
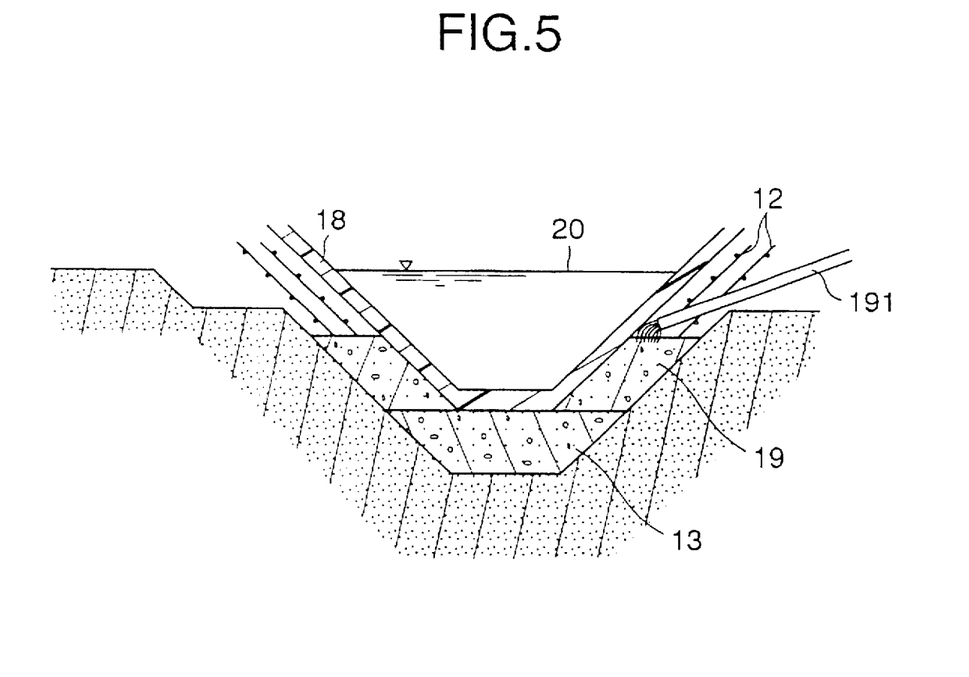
FIG. 5 is a longitudinal cross sectional view showing a part of the lower conical portion constructed by the method of the present invention.

The conical inside wall member 16 is used as a conical lower inside wall member 18 as shown in FIG. 5 and installed on the reinforcing bars 12 and the bottom concrete 13 as a formwork, and a lower concrete 19 is placed from a concrete pouring pipe 191. At the time, the conical lower inside wall member 18 is prevented from floating by being filled water 20 or sewage treated water which serves as a weight.

(2) Next, the execution of works for the cylindrical sidewall portion will be described.

Figure 6:
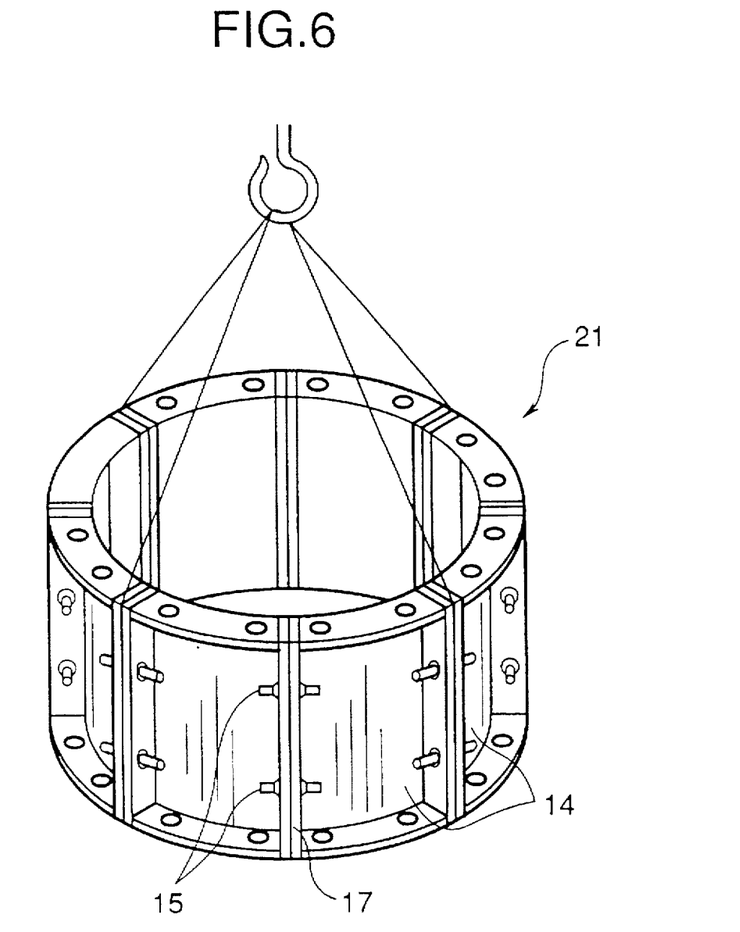
FIG. 6 is a perspective view showing a part of a sidewall cylindrical portion constructed by the method of the present invention.

As shown in FIG. 6, GFRU panels 14 are fabricated to a ring-shape using bolts 15, nails or an adhesive to thereby form cylindrical inside wall members 21. Joints 17 are sealed with a resin, tape or adhesive as shown in FIG. 4 described above.

Figure 7:
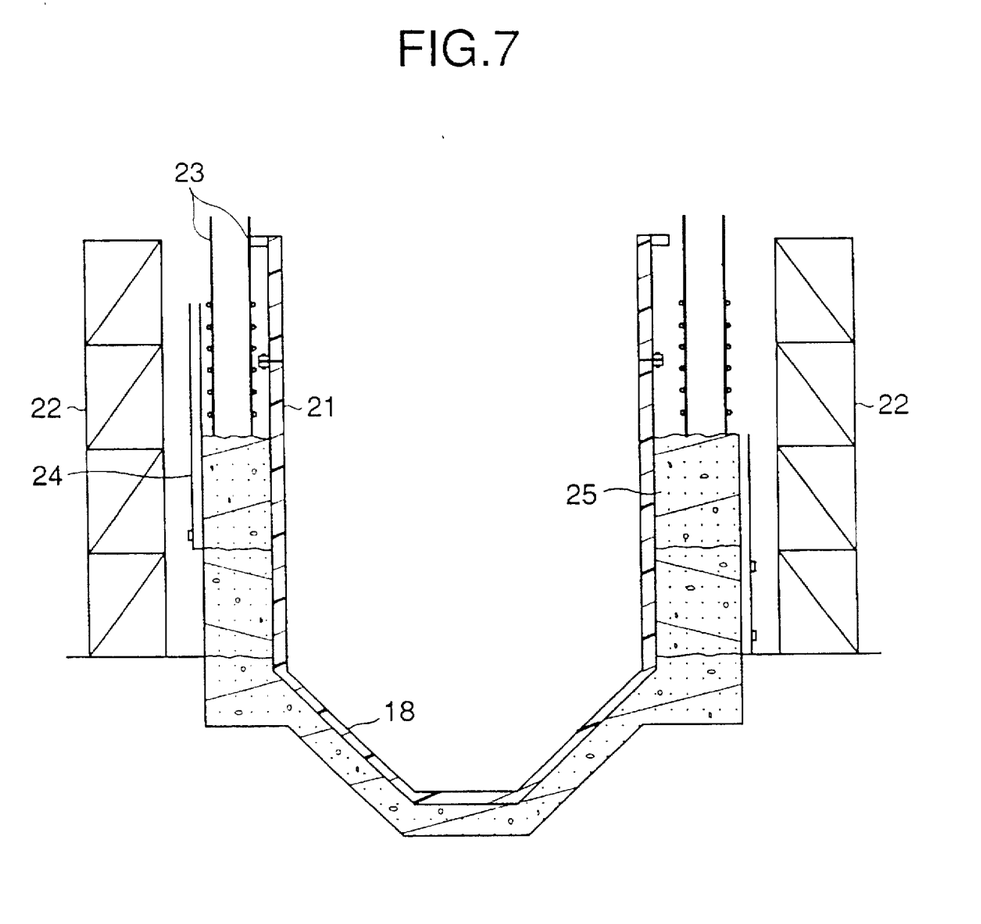
FIG. 7 is a longitudinal cross sectional view showing a part of the sidewall cylindrical portion constructed by the method of the present invention.

As shown in FIG. 7, the cylindrical inside wall members 21 are piled up and fabricated and used as an inside formwork. Sidewall reinforcing bars 23 are disposed using outside scaffolds 22, usual outside formworks 24 are disposed and a sidewall concrete 25 is placed.

(3) Next, the execution of works for the upper conical portion will be described.

Figure 8:
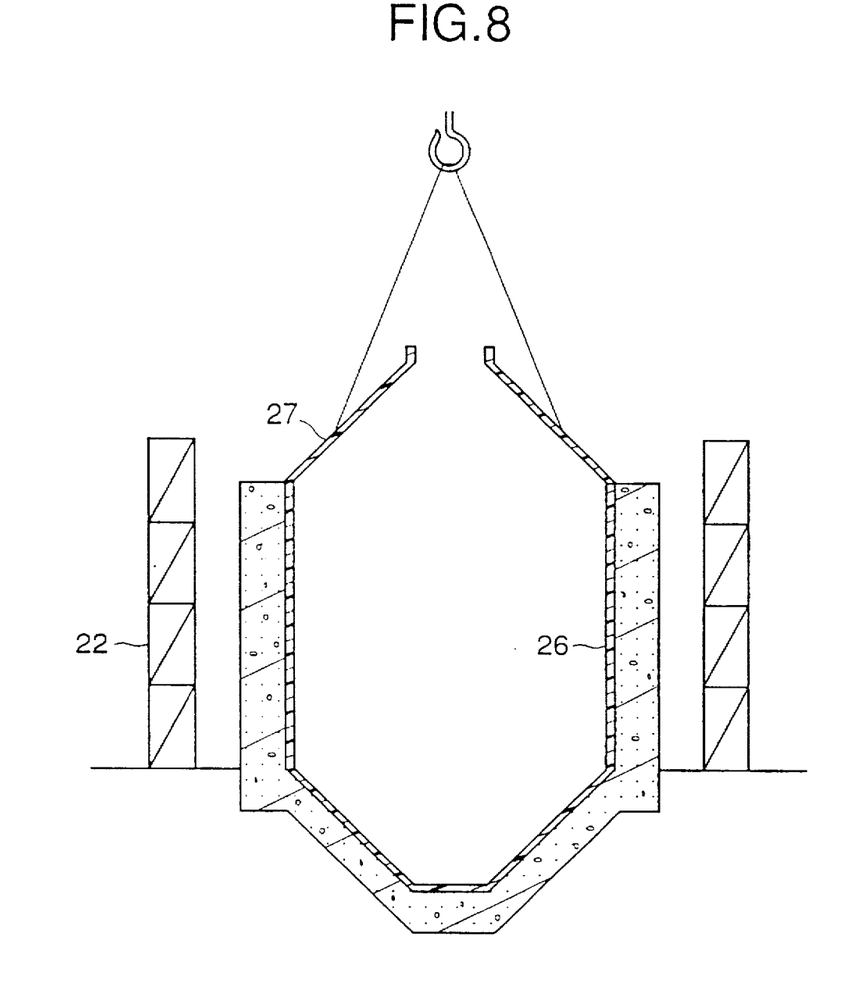
FIG. 8 is a longitudinal cross sectional view showing a part of an upper conical portion constructed by the method of the present invention.

As shown in FIG. 8, an upper inside wall member 27 is hung down and installed on a cylindrical sidewall portion 26 to which the sidewall concrete 25 has been placed. A member similar to the conical inside wall member 16 shown in FIG. 3 can be used as the upper inside wall member 27. When the upper inside wall member 27 has a weight exceeding the capacity of a crane, the GFRU panels 14 are divided into several sections and hung down and then fabricated.

Figure 9:
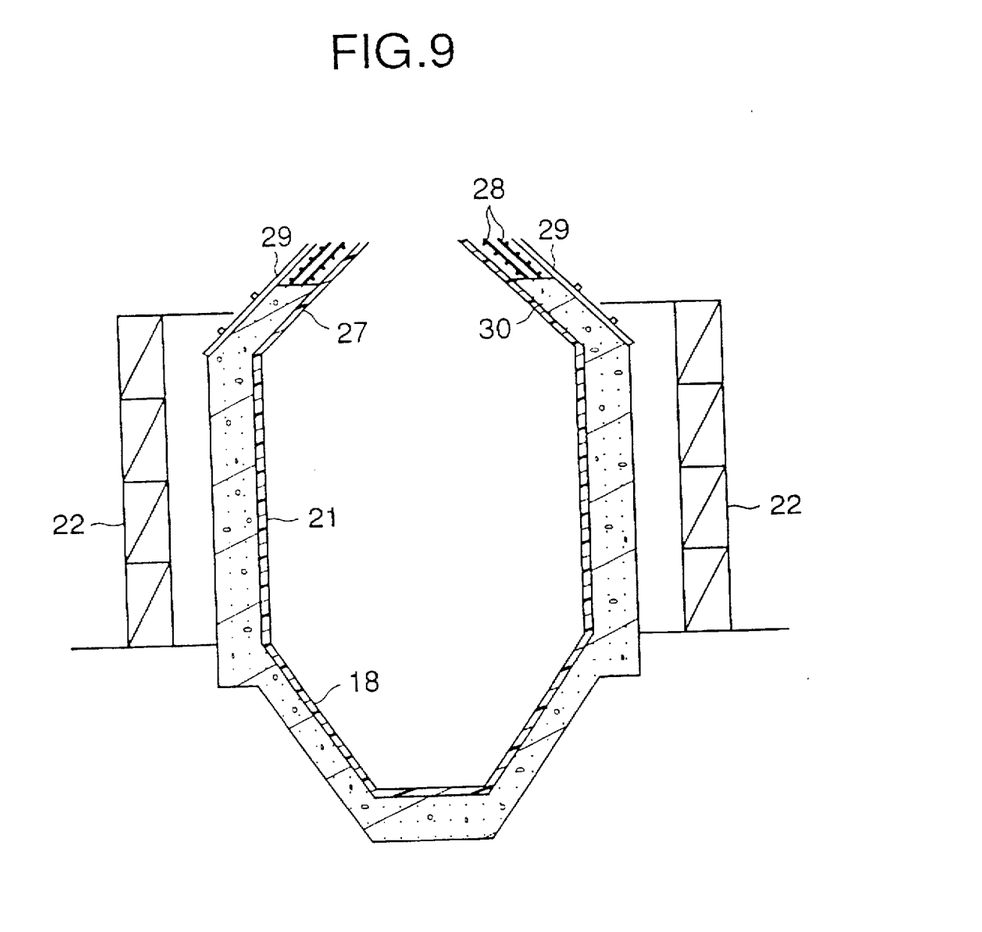
FIG. 9 is a longitudinal cross sectional view showing a part of the upper conical portion constructed by the method of the present invention.

Finally, the upper inside wall member 27 is used as an inside concrete placing formwork, upper reinforcing bars 28 are disposed as shown in FIG. 9, an upper concrete 30 is placed by installing an outside formworks 29, and then the outside formworks 29 and the outside scaffolds 22 are dismounted to thereby construct the digester tank 1 shown in FIG. 1.

According to the method as described above, the following advantages can be obtained:

(1) since a concrete work, insulating work and corrosion preventing work can be executed together at a time, a period of construction work can be greatly shortened;

(2) since a weather lining is not needed because the concrete is left in the placed state and further inside scaffolds can be omitted, a cost can be reduced;

(3) a good working environment can be provided by avoiding a bad working environment caused when a corrosion preventing agent is coated using thinner or the like; and (4) since the production of GFRU panels and the fabrication thereof can be previously executed in a factory, labor can be saved in construction works executed in a field.

As described above, according to the present invention, since a concrete work, insulating work and corrosion preventing work can be executed together at a time in the construction of a biological reaction tank such as a thickner tank, anaerobic sewage treatment tank, denitrification tank in addition to the digester tank, a period of construction work can be greatly shortened and further a construction cost can be reduced by the omission of weather linings and inside scaffolds.

What is claimed is:

1. In a method of constructing a concrete sludge treatment tank, an improvement comprising the step of using a member composed of a glass long-fiber reinforced foamed plastic composite material as an inside formworks of inside and outside formworks used to place concrete to said concrete sludge treatment tank.

2. A method of constructing a sludge treatment tank according to claim 1, wherein said inside formwork is used as an inside wall member of said sludge treatment tank after said concrete has been placed.

3. A method of constructing a sludge treatment tank according to claim 1, wherein said sludge treatment tank has any one of an egg-shaped longitudinal cross sectional shape and a hexagon-shaped longitudinal cross sectional shape, an upper portion and a lower portion thereof are formed to a substantially conical shape and a barrel thereof is formed to a cylindrical shape.

4. A method of constructing a sludge treatment tank according to claim 1, wherein said inside formworks are previously made to a predetermined shape in a factory and fabricated in a field.

5. A method of constructing a sludge treatment tank according to claim 1, wherein lower inside formworks of said sludge treatment tank are fabricated in the field, and the thus fabricated inside formworks is filled with any of water or sewage treated water to prevent said inside formworks from floating.

* * * * *

UNITED STATES PATENT AND TRADEMARK OFFICE
CERTIFICATE OF CORRECTION

PATENT NO. : 5,759,849
DATED : June 2, 1998
INVENTOR(S) : Aoyagi, et. al.

It is certified that error appears in the above-identified patent and that said Letters Patent is hereby corrected as shown below:

Title page, item [54] and col. 1, Title,

"SLUDGE TREATMENT TANK THEREOF CONSTRUCTION METHOD THEREOF"

should read

--SLUDGE TREATMENT TANK CONSTRUCTION METHOD--.

Signed and Sealed this

Twenty-second Day of September, 1998

Attest:

BRUCE LEHMAN

*Attesting Officer*  *Commissioner of Patents and Trademarks*